United States Patent
Pretz et al.

(10) Patent No.: US 10,392,319 B2
(45) Date of Patent: Aug. 27, 2019

(54) PROPANE DEHYDROGENATION SULFUR MANAGEMENT

(71) Applicant: Dow Global Technologies LLC, Midland, MI (US)

(72) Inventors: Matthew T. Pretz, Lake Jackson, TX (US); Lin Luo, Sugar Land, TX (US); Brien A. Stears, League City, TX (US); Mark W. Stewart, Pearland, TX (US)

(73) Assignee: Dow Global Technologies LLC, Midland, MI (US)

( * ) Notice: Subject to any disclaimer, the term of this patent is extended or adjusted under 35 U.S.C. 154(b) by 96 days.

(21) Appl. No.: 15/037,242

(22) PCT Filed: Dec. 3, 2014

(86) PCT No.: PCT/US2014/068271
§ 371 (c)(1),
(2) Date: May 17, 2016

(87) PCT Pub. No.: WO2015/094655
PCT Pub. Date: Jun. 25, 2015

(65) Prior Publication Data
US 2016/0289144 A1    Oct. 6, 2016

Related U.S. Application Data

(60) Provisional application No. 61/918,819, filed on Dec. 20, 2013.

(51) Int. Cl.
| | | |
|---|---|---|
| *C07C 5/333* | (2006.01) | |
| *C07C 7/12* | (2006.01) | |
| *C10G 25/00* | (2006.01) | |
| *C10G 35/09* | (2006.01) | |
| *C10G 9/00* | (2006.01) | |

(52) U.S. Cl.
CPC .............. *C07C 5/3337* (2013.01); *C07C 7/12* (2013.01); *C10G 9/00* (2013.01); *C10G 25/00* (2013.01); *C10G 35/09* (2013.01); *C07C 2521/12* (2013.01); *C07C 2523/04* (2013.01); *C07C 2523/08* (2013.01); *C07C 2523/42* (2013.01); *C07C 2523/62* (2013.01); *C07C 2527/224* (2013.01); *C10G 2400/20* (2013.01)

(58) Field of Classification Search
None
See application file for complete search history.

(56) References Cited

U.S. PATENT DOCUMENTS

| | | | |
|---|---|---|---|
| 3,808,324 A * | 4/1974 | Urban .................. | B01D 53/501 210/757 |
| 3,980,721 A * | 9/1976 | Juguin ..................... | B01J 23/64 585/430 |
| 4,080,394 A * | 3/1978 | Antos ...................... | C07C 5/325 585/434 |
| 4,238,366 A | 12/1980 | Antos | |
| 4,482,449 A | 11/1984 | Sorrentino et al. | |
| 5,157,201 A | 10/1992 | Norris | |
| 5,244,643 A | 9/1993 | Verachtert | |
| 5,723,707 A | 3/1998 | Heyse et al. | |
| 5,880,050 A * | 3/1999 | Boitiaux .................. | B01J 38/44 502/37 |
| 6,048,451 A | 4/2000 | Huff, Jr. et al. | |
| 7,201,839 B2 | 4/2007 | Turaga et al. | |
| 7,220,704 B2 | 5/2007 | Morton et al. | |
| 7,309,416 B2 | 12/2007 | Fokema et al. | |
| 2004/0242945 A1* | 12/2004 | Pelati ....................... | B01J 23/08 585/444 |
| 2008/0051618 A1* | 2/2008 | Kim ......................... | B01J 23/62 585/431 |
| 2008/0194891 A1* | 8/2008 | Pretz ..................... | C07C 5/3332 585/252 |

(Continued)

FOREIGN PATENT DOCUMENTS

| | | |
|---|---|---|
| CN | 102380426 | 6/2013 |
| EP | 0637578 A1 | 2/1995 |

(Continued)

OTHER PUBLICATIONS

Rennard, R.J. et al., in "The role of sulfur in deactivation of Pt/MgAl2O4 for propane dehydrogenation", Journal of Catalysis 98, 235-244 (1986).
Chaiyavech, P, "Commercialization of the World's First Oleflex Unit", The Journal of the Royal Institute of Thailand, vol. 27 No. 3, Jul.-Sep. 2002, pages.
Radzi et al., "Kinetic model and Simulation Analysis for Propane Dehydrogenation in an Industrial Moving Bed Reactor", World Academy of Science, Engineering and Technology 52, 2011, pp. 183-189.
"Greenhouse Gas PSD Permit Application, C3 Petrochemicals LLC Propane Dehydrogenation Unit, Chocolate Bayou Plant, Alvin Texas" prepared by ENVIRON International Corporation, Feb. 2013, Project No. 31-30172C, pp. 1 to C9.
Siddiqui et al, Applied Catalysis A: General 303, "Sulfur reduction in FCC gasoline using catalyst additives", (2006) 116-120.

(Continued)

*Primary Examiner* — Philip Y Louie
(74) *Attorney, Agent, or Firm* — Dinsmore & Shohl LLP

(57) ABSTRACT

Manage sulfur present as sulfur or a sulfur compound in a hydrocarbon feedstream while effecting dehydrogenation of hydrocarbon(s) (e.g. propane) contained in the hydrocarbon feedstream to its/their corresponding olefin (e.g. propylene where the hydrocarbon is propane) without subjecting the feedstream to desulfurization before it contacts a fluidizable dehydrogenation catalyst that is both a desulfurant and a dehydrogenation catalyst and comprises gallium and platinum on an alumina or alumina-silica catalyst support with optional alkali or alkaline earth metal such as potassium. Contact with such a catalyst yields a desulfurized crude olefin product that corresponds to the hydrocarbon and has a reduced amount of sulfur or sulfur compounds relative to the sulfur or sulfur compounds present in the hydrocarbon feedstream prior to contact with the catalyst.

17 Claims, No Drawings

(56) References Cited

U.S. PATENT DOCUMENTS

| | | | |
|---|---|---|---|
| 2010/0236985 A1* | 9/2010 | Luo | B01J 23/62 208/138 |
| 2011/0033370 A1 | 2/2011 | Ayala et al. | |
| 2012/0000827 A1 | 1/2012 | Krupa et al. | |
| 2012/0043225 A1 | 2/2012 | Zhou et al. | |
| 2012/0046188 A1 | 2/2012 | Berland et al. | |
| 2013/0252801 A1* | 9/2013 | Leonard | B01J 23/96 502/53 |
| 2016/0289144 A1 | 10/2016 | Pretz et al. | |

FOREIGN PATENT DOCUMENTS

| | | | |
|---|---|---|---|
| JP | 2006036616 A | | 2/2006 |
| KR | 20090052864 | | 5/2009 |
| KZ | 24938 B | | 11/2011 |
| RU | 2128551 C1 | | 4/1994 |
| WO | 2002012152 A1 | | 2/2002 |
| WO | 2013009820 A1 | | 1/2013 |

OTHER PUBLICATIONS

International Search Report and Written Opinion dated Mar. 4, 2015.

International Preliminary Report on Patentability dated May 2, 2016.

EP Examination Report pertaining to 14816050.0 dated Jun. 29, 2017.

Chinese Third Office Action and Search Report dated Aug. 8, 2018 pertaining to Chinese Patent App. No. 201480068044.6, 5 Pages.

Decision to Grant issued by the Russian Patent Office for Russian Application No. 2016129141 dated Dec. 14, 2018 (14 pages).

* cited by examiner

PROPANE DEHYDROGENATION SULFUR MANAGEMENT

The present application claims the benefit of U.S. Provisional Application No. 61/918,819, filed on Dec. 20, 2013.

This invention relates generally to management of sulfur levels in a hydrocarbon stream, either an alkyl stream (also known as "alkanes") or an aromatic stream (e.g. ethylbenzene), that is processed using a circulating fluid bed reactor to convert the hydrocarbon stream to a product stream. It relates more particularly to hydrocarbon streams that have a sulfur level of less than 1000 parts by weight per million parts by weight (ppm) of the hydrocarbon stream. It relates still more particularly to using at least a portion of a supported catalyst material as a sulfur absorbent in said circulating fluid bed reactor.

U.S. Pat. No. 7,220,704 (Morton et al.) relates to removal of sulfur from hydrocarbon streams as well as desulfurization of fluid streams of cracked gasolines and diesel fuels and a novel composition for the same. The desulfurized cracked gasoline contains less than 100 ppm sulfur, preferably less than 50 ppm sulfur. The composition comprises a) a metal oxide selected from a gallium oxide ($Ga_2O_3$), an indium oxide or a combination of any two or more thereof, b) a silicon-containing material, c) an aluminum-containing material, and d) a promoter, at least a portion thereof being present as a reduced valence promoter. Promoters include at least one metal, metal oxide, metal oxide precursor, solid solution of more than metal, or an alloy of more than metal, wherein the metal is selected from nickel (Ni), cobalt (Co), iron (Fe), manganese (Mn), copper (Cu), zinc (Zn), molybdenum (Mo), tungsten (W), silver (Ag), tin (Sn), antimony (Sb), vanadium (V), gold (Au), platinum (Pt), ruthenium (Ru), iridium (Ir), chromium (Cr), palladium (Pd), titanium (Ti), zirconium (Zr), rhodium (Rh), rhenium (Re), and combinations of any two or more thereof.

U.S. Pat. No. 7,201,839 (Turaga et al.) teaches desulfurization and a composition for the same that comprises a metal oxide, a silica-containing material, a Ga-containing material, an aluminum (Al)-containing material selected from alumina, aluminate and combinations thereof, and a promoter, with at least a portion of the promoter being present as a reduced valence promoter (an oxide of a metal selected from Zn, Mn, Ag, Cu, cerium (Ce), scandium (Sc), lanthanum (La), Fe, Sn, cadmium (Cd), gallium (Ga), indium (In), niobium (Nb), tantalum (Ta) or a combination of two or more of such metals). The composition is used in a desulfurization zone to remove sulfur from a hydrocarbon stream such as cracked gasolines and diesel fuels.

U.S. Pat. No. 5,723,707 (Heyse et al.) relates to dehydrogenation processes, especially dehydrogenation of hydrocarbons (two to thirty or more carbon atoms) with an emphasis on light hydrocarbons such as dehydrogenation of propane to form propylene, equipment and catalyst loads therefore. Heyse et al. refers to conventional dehydrogenation techniques using feeds that have a sulfur loading of e.g. 50-100 ppm and notes that carburization (forming carbon deposits) does not appear to be a problem at those loadings. Heyse et al. focuses on minimizing problems with carburization by providing a metallic protective layer, especially a stannide protective layer, to metal surfaces that impart long-term carburization, embrittlement, coking and metal-dusting protection at dehydrogenation temperatures. Heyse et al. also contemplates adding sulfur as a means of combating carburization, noting that the coatings can tolerate up to 200 ppm sulfur in a feedstream. The hydrocarbon may be in a liquid phase, a mixed vapor-liquid phase or the vapor phase when it contacts the catalytic composite, but is preferably in the vapor phase.

USPP 2011/0033370 (Ayala et al.) relates to a system and method for sulfur recovery in the production of sulfur from a sulfur-laden gas. Ayala et al. notes that one process of removing sulfur compounds from a sulfur-laden gas stream includes desulfurization through contact of sulfur compounds with a sorbent such as a metal oxide to form metal sulfides (also known as a sulfurized mass). Sorbent materials can include transition metals such as Cu, Zn, Fe, Ni, Cr, V, W or mixtures thereof and alkaline earth metals as well as metal oxides such as iron oxide, zinc oxide, zinc ferrite, copper ferrite, copper oxide, vanadium oxide, and mixtures thereof, and zinc titanate.

Canadian Patent Application (CA) 2,525,824 (Fokema et al.) provides methods and compositions for desulfurization of hydrocarbon fuels. The methods include sulfur removal from a hydrocarbon fuel via contact with a desulfurization agent such as a transition metal oxide like molybdenum oxide in the absence of added hydrogen.

Patent Cooperation Treaty Publication (WO) 92/00261 (Norris) discloses a method of removing sulfur components from a hydrocarbon stream by contacting the stream that has an initial amount of a sulfur species with a catalyst capable of adsorbing the sulfur species in the absence of extraneously added hydrogen. The catalyst, also called an adsorbent material, is in particulate form and includes either unsupported metal oxides or metal oxides on an inert support. Suitable metal oxides are selected from cobalt oxide, nickel oxide, molybdenum oxide, zinc oxide and copper oxides and mixtures thereof.

R. J. Rennard et al., in "The role of sulfur in deactivation of $Pt/MgAl_2O_4$ for propane dehydrogenation", *Journal of Catalysis* 98, 235-244 (1986) notes, in part, that trace amounts of sulfur in a dehydrogenation feedstream (25 to 500 ppm) suppress both hydrogenolysis and coke formation.

Conventional dehydrogenation catalysts often suffer from deactivation by coking when operating at preferred temperatures to push the reaction equilibrium. This necessitates burn off of carbon to maintain catalyst activity. In the Catofin™ process, one typically swaps the entire bed in order to burn off this coke which also supplies the necessary heat of reaction. In other processes, such as Oleflex™, sulfur compounds present in the feedstream are removed and then specific sulfur compounds and hydrogen are introduced into the reactor feed to control the rate of carbon build-up in the reactor. See, e.g., U.S. Pat. No. 5,723,707; P. Chaiyavech, "Commercialization of the World's First Oleflex Unit", *The Journal of the Royal Institute of Thailand*, Vol. 27 No. 3, July-September 2002, pages ; and Chin S. Y. Radzi et al., "Kinetic model and Simulation Analysis for Propane Dehydrogenation in an Industrial Moving Bed Reactor", World Academy of Science, Engineering and Technology 52, 2011, pages 183-189; and "Greenhouse Gas PSD Permit Application, C3 Petrochemicals LLC Propane Dehydrogenation Unit, Chocolate Bayou Plant, Alvin Tex." prepared by ENVIRON International Corporation, February 2013, Project Number 31-30172C, pages 1 to C9.

In some aspects, this invention is a method for managing sulfur present as sulfur or a sulfur compound in a hydrocarbon feedstream while effecting dehydrogenation of the hydrocarbon contained in the hydrocarbon feedstream, the method comprising placing the hydrocarbon feedstream in contact with a fluidizable catalyst that is both a desulfurant and a dehydrogenation catalyst and comprises gallium in an amount within a range of from greater than 0 percent by weight to 5 percent by weight (wt %), and platinum in an amount within a range of from greater than 1 to 300 parts by weight per million parts by weight (ppm) of the catalyst on an alumina or alumina-silica catalyst support optionally with 0.01 to 5 percent by weight, preferably 0.05 to 1 percent by weight of alkali and/or earth-alkaline metals such as potassium, in each case based upon weight of the catalyst, under conditions sufficient to effect both removal from the hydrocarbon feedstream of at least a portion of the sulfur or sulfur compound contained therein, the amount of sulfur or sulfur compound in the feedstream prior to contact with the catalyst being within a range of from at least 1 part by weight per million parts by weight of feedstream to less than 1000 parts by weight per million parts by weight (ppm) of feedstream, and dehydrogenation, preferably concurrent dehydrogenation, of the hydrocarbon to yield a desulfurized crude olefin product that corresponds to the hydrocarbon; the desulfurized crude olefin product containing a reduced amount of sulfur or sulfur compounds relative to the sulfur or sulfur compounds present in the hydrocarbon feedstream prior to contact with the catalyst.

As used herein, an alumina-silica catalyst support, sometimes referred to as a silica-modified alumina support, preferably has a silica content within a range of from greater than 0 wt % to less than 10 wt %, based on total weight of the support. A silica-modified alumina support is not a zeolite.

As used herein, "adsorbent/catalyst" refers to a material that functions as either or both of a catalyst and as an adsorbent. Any reference to catalyst or adsorbent or catalyst/adsorbent is interchangeable with no loss of meaning or scope.

In some aspects, this invention further comprising sequential steps of a) effecting separation of the desulfurized crude olefin product from the catalyst onto which at least a portion of the sulfur is absorbed; and b) subjecting at least a portion of such catalyst to regeneration with air as a regeneration gas.

The amount of sulfur or sulfur in the feedstream prior to contact with the catalyst causes a drop in catalyst dehydrogenation activity over an average catalyst residence time within a range of from 0.1 minute to 10 minutes of less than 30 percent versus a case with no sulfur in the feed as measured by the method using fixed bed experiments described later in this report for sulfur concentrations ranging up to 123 ppm wt total sulfur. The sulfur compound(s) can be in many forms which may include $H_2S$, methyl mercaptan, and/or COS.

The reduced amount of sulfur or sulfur compound in the crude olefin product is generally less than 50%percent, preferably less than 5%, of the amount of sulfur or sulfur compound in the feedstream prior to contact with the adsorbent/catalyst, hereinafter primarily referred to as "catalyst". The removal rate depends upon, among other factors, the level of impurities, reactor design, regenerator design and operating conditions Sulfur management in accord with this invention includes a combination of a catalyst that tolerates sulfur levels discussed herein and steps needed to remove and desirably separate and recover sulfur and/or sulfur compounds from a feedstream so as to yield the desulfurized crude olefin product noted above. The method of this invention does not include pre-treatment steps wherein sulfur is removed from the feedstream before it contacts the catalyst. By way of contrast, this invention includes steps to continuously remove sulfur and/or sulfur compounds after the feedstream contacts the catalyst, preferably in a regenerator or regeneration zone by, for example, oxidation. "Continuously" means that the catalyst operates in a continuous mode rather than a batch mode to remove sulfur components from the catalyst at steady state with less than 10 minutes of average catalyst residence time in the reactor/adsorber. Batch modes or batch processes typically require the use of fixed bed reactors that must be swapped online, an action that causes downstream process interruptions and may adversely impact failure prone high temperature switching valves.

The fluidizable catalyst comprises gallium in an amount within a range of from greater than 0 percent by weight (wt %) to 5 wt %, and preferably from 1 wt % to 2 wt % and platinum in an amount within a range of from greater than 1 part by weight per million parts by weight (ppm) to 500 ppm, preferably from 20 ppm to 300 ppm of the catalyst on an alumina or alumina-silica catalyst support and optionally with 0.01 wt % to 5 wt %, preferably 0.05 wt % to 1 wt % of alkali and/or earth-alkaline metals such as potassium. The method of this invention yields satisfactory results with a catalyst support that is alumina-silica with an alumina content within a range of from 90 to 99.5 wt % and a silica content within a range of from 0.5 to 10 wt %, both percentages being based upon total catalyst support weight and, when added together, total 100 wt %. The alumina content is preferably within a range of from 97 wt % to 99.5 wt % and the silica content is preferably within a range of from 0.5 wt % to 3 wt %, both percentages being based upon total catalyst support weight and totaling 100 wt % when added together.

As used herein, an "upflow" or "upward flow" reactor is a reactor in which the average velocity of the catalyst and/or gas over a given cross section of the reactor is in the upward direction so as to provide a net upward flow of catalyst and gases. This type of reactor can operate in a dilute phase pneumatic conveying condition such as a riser reactor, a fast fluidized reactor, a turbulent bed reactor or a bubbling bed reactor. In addition, multiple types of reactors can be combined to form a single upflow reactor. For example, a riser reactor might operate at superficial gas velocities ranging from 30 feet per second (ft/s) (9.14 meters/second (m/s)) to 80 ft/s (24.4 m/s). A fast fluidized or turbulent bed reactor might operate at superficial gas velocities ranging from 2 ft/s (0.6 m/s) to 10 ft/s (3.5 m/s) and a bubbling bed reactor might operate at superficial gas velocities ranging from 0.05 ft/s ($1.5 \times 10^{-2}$ m/s) to 4 ft/s (1.2 m/s) depending on process conditions and catalyst flux. Some of these reactors may operate with both the gas and catalyst in a more plug flow condition such that the catalyst and gas backmix to some degree, but one can still observe temperature profiles in the reactor due to the endothermic nature of the dehydrogenation reaction. Alternatively, as gas velocity drops, solids phase back mixing increases to a point that the solids phase approaches isothermal behavior. The gas may be more plug flow than the solid, but it may also achieve higher levels of back-mixing.

The method of this invention includes several desirable operating parameters. The method includes a temperature within a range of from 550 degrees centigrade (° C.) to 800° C., preferably from 585° C. to 750° C., and a pressure within a range of from 3.6 pounds per square inch absolute (psia) (24.8 kilopascals (KPa) to 64.7 psia (446.1 KPa), preferably from 8 psia (55.1 KPa) to 40 psia (275.8 KPa) depending on the chemistry and economics for each particular feed stream. The feedstream for the method includes at least one of an alkane or an alkyl aromatic, with an alkane that contains from 2 carbon atoms to 4 carbon atoms being preferred, and propane being most preferred. The method operates with a superficial velocity that ranges from 1 foot per second (ft/sec) (0.3 meter per second (m/s)) to 80 ft/sec (24.4 m/s). Calculate superficial velocity by dividing volumetric flowrate of a gas at any point in the reactor by cross-sectional area of the reactor at that point. The method also operates with a catalyst flux that ranges from 0.1 pound/square foot per second (lb/ft$^2$-sec) (0.5 kg/m$^2$ sec) to 100 lb/ft$^2$-sec) (488 kg/m$^2$-sec). Calculate catalyst flux by either multiplying solids velocity by its apparent density or dividing solids mass rate by cross-sectional area of the reactor at that point.

Other operating parameters for the method of this invention include an average gas residence time (GRT) while at reaction temperature within a range of from 0.1 second (s) to 10 s, preferably from 2 s to 8 s, an average catalyst residence time within the reactor of from 1 s to 600 s, preferably from 5 s to 200 s, a reactor apparent catalyst density within a range of from 0.1 pound per cubic foot (lb/ft$^3$) (0.016 grams per cubic centimeter (g/cm$^3$)) to 65 lb/ft$^3$ (1.04 g/cm$^3$), and a weight hourly space velocity (WHSV) within a range of from 0.1 to 1000, preferably from 0.5 to 25. WHSV is defined as mass rate (mass per unit time such as pounds per hour (lb/hr)) of hydrocarbon feed to the reactor divided by mass of catalyst in the reactor. The mass of catalyst in the reactor is equal to the apparent density of the catalyst in the reactor multiplied by reactor volume. The reactor volume is a function of capacity. The gas residence time limitations enable the reactor volume to be calculated for a given plant capacity.

An additional operating parameter is catalyst/hydrocarbon feed ratio, defined as mass rate of catalyst in the reactor in pounds per hour (lb/hr) (kilograms per hour (kg/hr)) divided by mass rate of hydrocarbon being fed to the reactor in lb/hr or kg/hr, as appropriate to yield a dimensionless number. Catalyst/hydrocarbon feed ratios suitable for this invention range from 1 to 100, preferably from 5 to 50.

In some aspects of this invention, approximately 50% of sulfur and sulfur compounds (e.g. hydrogen sulfide, methyl mercaptan and carbon oxysulfide (COS)) that enters the reactor as part of a feed stream will be absorbed to the catalyst and effectively later removed from the catalyst in the regenerator through an oxidation process. Some fraction of feed stream sulfur is expected to exit the reactor and its associated components (also known as a "reaction system") and proceed to a finishing system for removal or recovery of at least a portion of such sulfur. In some dehydrogenation cases (e.g. propane to propylene), one may use an optional caustic tower as a means to remove remaining portions of such sulfur compounds. The sulfur species will exit the bottoms of the caustic tower in the liquid phase in various forms of sulfur that will be processed with conventional sulfur management techniques.

A portion of, or in some cases all of, the catalyst exiting the reactor desirably enters a regenerator which is heated by a combination of combustion of carbonaceous material (coke) formed on the catalyst during dehydrogenation and combustion of a supplemental fuel such as natural gas, methane, hydrogen, ethane or another combustible hydrocarbon to a temperature within a range of from 550° C. to 800° C., preferably from 660° C. to 780° C. Pressure within the regenerator ranges from 14.7 pounds per square inch absolute (psia) (101.4 KPa) to 84.7 psia (584 KPa). Subsequent to such combustion, the catalyst is preferably subjected to an oxygen-containing gas for a period of more than two minutes as taught in co-pending application PCT/US012/046188. Combustion can occur in a counter flow bubbling bed system or in an upflow reactor with a net upward flow of catalyst and gases. The combustor operates with a weight hourly space velocity within a range of from 0.5 hr$^{-1}$ to 1000 hr$^{-1}$ as calculated by the sum of the mass of air and fuel divided by the mass of adsorbent/catalyst in the combustion area only. The combustion section is then followed by the subsequent greater than 2 minutes of oxygen containing gas which can operate in an upflow or counterflow configuration but preferentially counterflow. Counterflow is defined as the net catalyst velocity moving downward and the net air velocity moving upward.

Operation of the regenerator within the above noted parameters effectively removes from the catalyst at least a portion of sulfur and sulfur compounds (e.g. hydrogen sulfide, methyl mercaptan and carbon oxysulfide (COS)) deposited, absorbed or adsorbed thereon during dehydrogenation within the reactor. Complete removal of such sulfur and sulfur compounds, while theoretically possible, is not necessary as long as enough sulfur and/or sulfur compounds is/are removed from the catalyst such that it continues to function as both a dehydrogenation catalyst and a desulfurant when it is recycled to the reactor.

In some aspects of this invention, sulfur and/or sulfur compounds exiting the regenerator proceed to a finishing system for recovery thereof. Sulfur species that are removed from the catalyst within the regenerator tend to leave the regenerator as sulfur oxides (SOx). The SOx contained in regenerator effluent can either be released directly to atmosphere if environmental regulations permit doing so or placed in contact with a suitable scrubbing agent such as caustic that removes SOx from regenerator effluent. In the latter instance, resulting sulfur species tend to be in liquid phase and may be treated in accord with conventional sulfur management techniques.

The sulfur or sulfur in the feedstream is believed to cause a drop in catalyst dehydrogenation activity. For a typical commercial propane stream with 13 ppmw sulfur in the form of methyl mercaptan and 2 ppmw sulfur in the form of COS, the overall (accumulative) propane conversion can drop 6% to 24% relative to the propane conversion obtained from a sulfur free feed when cat/oil ratio varies from 36 to 5. This loss can be reduced when a promoter metal is incorporated into the catalyst system. Illustrative promoter metals include Zn, Mo, and Cu, with Zn being preferred. Promoter metal loading desirably ranges from 10 ppm to 1000 ppm, more preferably from 10 ppm to 200 ppm, based upon catalyst/absorber weight. As used herein, adsorption includes both chemical (chemisorption) and physical (physisorption) processes where a substrate, compound or material is distributed on a surface of an adsorbent. Chemisorption includes formation of new chemical bonds (covalent or ionic) between the surface of the adsorbent and the substrate. Physisorption includes interaction of the substrate and the surface via van der Waals and other electrostatic forces. Absorption is a physical or chemical phenomenon or a process in which atoms, molecules, or ions enter a bulk phase—gas, liquid, or solid material. The absorbent distributes the material it captures throughout its entire matrix or volume.

In addition, sulfur species may enter the fluidized system and chemically break down into more stable products which then adsorb to the surface of the catalyst. For example, methyl mercaptan and COS may thermally degrade or react to form $H_2S$ which adsorbs to the adsorbent/catalyst.

COMPARATIVE EXAMPLE (CEX) A

Pass a feed stream through a quartz reactor that is filled only with quartz chips (no catalyst) and heated to a temperature of 625° C. under ambient pressure at a flow rate of 51.4 standard cubic centimeters per minute (sccm). The feed stream has a composition of 120 moles per million moles of feedstream (ppmmol) $H_2S$, 90 mole % propane, and 10 mole % $N_2$. Collect gas exiting the reactor ("effluent gas") using a 1L gas bag and subject the collected gas to analysis using a Draeger tube (GasTech tube type 4LL). The analysis shows that the effluent contains approximately 116 ppm sulfur, an indication of essentially no $H_2S$ adsorption in the absence of a catalyst.

EXAMPLE (EX) 1

Replicate CEx A, but add 0.5 g Pt—Ga—K catalyst (73 ppm Pt, 1.5 wt % Ga, 0.22 wt % K supported on alumina with 1.5 wt % silica (Siralox 1.5/70, Sasol)) with the quartz chips. Analysis of effluent gas shows no detectable amount of sulfur, an indication that the catalyst adsorbed all of the $H_2S$ from the feed stream. The Catalyst to Oil (wt/wt) ratio corresponding to 5 min on stream with feed flow rate of 51.4 sccm is 1.2.

Dehydrogenation/Catalyst Reactivation/Catalyst Rejuvenation Procedure

Admix 0.5 g of the Ex 1 catalyst with 1.0 g silicon carbide, then subject the catalyst to a number of dehydrogenation reaction step/catalyst reactivation step/catalyst rejuvenation step cycles as detailed below. In the dehydrogenation reaction step, pass a propane feed stream through the catalyst for a period of 120 seconds at a temperature of 625° C. and a propane WHSV of 10 reciprocal hours ($hr^{-1}$) under ambient pressure. Collect data for propane conversion and propane selectivity either by GC at about 17 sec after initiating contact between the feed stream and the catalyst (time-on-stream) (Example 3) or by Mass Spectroscopy (Prima) (Example 2) approximately every 5 seconds. After the 120 second period lapses, ramp reactor temperature to 750° C. at a rate of 20° C. per minute in the presence of helium (He) flowing through the catalyst at a rate of 120 sccm. Maintain the temperature at 750° C. while contacting the catalyst with a stream composed of 4 mol % oxygen, 8 mol % carbon dioxide, 16 mol % water vapor and 72 mol % helium (He) at a flow rate of 150 sccm for a period of three minutes followed by passing 100% air through the catalyst at a flow rate of 150 sccm for a period of 15 minutes. After the air treatment pass He through the system at 120 sccm for 20 minutes while the reactor changes temperature from 750° C. to 625° C. before passing the propane feed stream through the catalyst to begin the next cycle.

EX 2 AND CEX B

Evaluate dehydrogenation performance of the Pt—Ga—K catalyst using two propane feed streams, one without sulfur (Base Feed), and one with approximately 15 ppm sulfur (Feed A). The Base Feed comprises 90 mol % high purity propane (Airgas, 99.5% purity propane) and 10 mol % nitrogen, both mol % being based on total moles of propane and nitrogen. Feed A contained 15 ppm sulfur in a feed with composition 89 mol % propane, 4.6 mol % ethane, 0.9% C4s, and 5.36 mol % nitrogen, each mol % being based upon total moles of propane, ethane, C4s and nitrogen. The two feed streams have equivalent propane partial pressure and overall space velocity during testing.

Table 1 below shows snap shots of propane conversion collected during a dehydrogenation step in the reaction/regeneration cycles. Time-on-stream means the length of time the catalyst is under a propane feed after the initial contact between the feed stream and the catalyst. Cat/Oil (wt/wt) ratio is calculated as the weight of catalyst divided by the total weight of propane effected on catalyst at a specified time-on-stream. The calculated accumulative conversion in Table 1 refers to the total % of propane converted from the initial contact of catalyst and feed to the specified time on stream of the catalyst. The data in Table 1 shows that although there is a negative impact of sulfur on catalyst performance, the impact on accumulative propane conversion is low at Cat/Oil larger than 6. For example, the loss in accumulative propane conversion is 5.6% at Cat/Oil of 12.0 when 15 ppm of sulfur was present. The data also shows a reduced propane conversion for any feed with increased catalyst time-on-stream, with a higher deactivation rate under Feed A in which sulfur is present. The difference in activity reduction is in line with sulfur adsorption on catalyst for Feed A. This conversion loss during the dehydrogenation step can be recovered with a regeneration step. After catalyst regeneration, the snapshot conversion at TOS of 10 sec in the dehydrogenation step of the next cycle returns back to around 50.5% and 46.5% for Base Feed and Feed A, respectively. The recovery of catalyst activity loss resulting from exposure to a sulfur containing feed provides indirect evidence that sulfur based materials are removed from the catalyst by regeneration.

TABLE 1

Comparison of propane conversion with Base Feed and Feed A.

| Time-on-stream, (TOS) sec | Base Feed | | Feed A | | Delta | |
|---|---|---|---|---|---|---|
| | Snap Shot Conv. | Accumulative Conv. | Snap Shot Conv. | Accumulative Conv. | Accumulative Conv. | Cat/Oil (wt/wt) |
| 10 | 50.5% | 52.0% | 46.5% | 49.1% | 2.9% | 36.0 |
| 20 | 46.5% | 50.2% | 39.5% | 46.0% | 4.2% | 18.0 |
| 30 | 43.1% | 48.4% | 33.4% | 42.8% | 5.6% | 12.0 |
| 40 | 40.1% | 46.7% | 28.1% | 39.7% | 6.9% | 9.0 |
| 50 | 37.6% | 45.1% | 23.6% | 36.9% | 8.2% | 7.2 |
| 60 | 35.3% | 43.6% | 19.7% | 34.4% | 9.3% | 6.0 |
| 70 | 33.3% | 42.3% | 16.5% | 32.0% | 10.3% | 5.1 |

EXAMPLE 3

Due to the low sulfur content involved, measurement of sulfur in the regeneration stream or sulfur on catalyst is challenging and leads to an alternate approach as detailed herein. Table 2 shows propane conversion at 17 sec TOS with Feed A and subsequently with Base Feed after feed switching. The data for Feed A shows performance of the last four cycles under this feed after ninety eight (98) cycles. The catalyst activity under Feed A is equivalent from cycle to cycle (only four cycles are shown), suggesting that there is no continuous accumulation of sulfur on catalyst after multiple cycles and the amount of sulfur deposited on catalyst during the dehydrogenation step is at least partially removed from the catalyst during the catalyst regeneration. After switching to the Base Feed, the propane conversion starts to climb up and reaches a plateau within six cycles. This Example 3 provides at least indirect evidence that adsorbed sulfur on catalyst is released during regeneration.

TABLE 2

Propane conversion and propylene selectivity collected at ~17 sec TOS after a feed switch from Feed A to Base Feed.

| Feed | No. of Cycles | Propane Conv. | Propylene Sel. |
|---|---|---|---|
| Feed A | 1 | 46.7% | 96.5% |
|  | 2 | 46.2% | 96.6% |
|  | 3 | 46.5% | 96.7% |
|  | 4 | 46.3% | 96.6% |
| Base Feed | 1 | 46.3% | 96.3% |
|  | 2 | 47.7% | 96.4% |
|  | 3 | 47.9% | 96.4% |
|  | 4 | 48.2% | 96.3% |
|  | 5 | 48.4% | 96.4% |
|  | 6 | 48.5% | 96.4% |
|  | 7 | 48.5% | 96.5% |
|  | 8 | 48.6% | 96.5% |
|  | 9 | 48.7% | 96.4% |
|  | 10 | 48.6% | 96.4% |

What is claimed is:

1. A method for reducing sulfur present as sulfur or sulfur compounds in a hydrocarbon feedstream while effecting dehydrogenation of the hydrocarbon contained in the hydrocarbon feedstream, the method comprising:

contacting the hydrocarbon feedstream with a fluidizable catalyst at a catalyst to hydrocarbon feed ratio in a range of from 1 to 100 under conditions sufficient to effect both removal from the hydrocarbon feedstream of at least a portion of the sulfur or sulfur compounds contained in the hydrocarbon feedstream and dehydrogenation of the hydrocarbon to yield a desulfurized crude olefin product, wherein:

a residence time of the fluidizable catalyst in contact with the hydrocarbon feedstream is from 0.1 minutes to 10 minutes;

the fluidizable catalyst is both a desulfurant and a dehydrogenation catalyst and comprises gallium in an amount within a range of from greater than 0 percent by weight to 5 percent by weight, and platinum in an amount within a range of from greater than 1 to 300 parts by weight per million parts by weight of the fluidizable catalyst on an alumina or alumina-silica catalyst support;

an amount of sulfur or sulfur compounds in the hydrocarbon feedstream prior to contact with the fluidizable catalyst is within a range of from at least 1 part by weight per million parts by weight of the hydrocarbon feedstream to less than 1000 parts by weight per million parts by weight of the hydrocarbon feedstream; and the desulfurized crude olefin product comprises a reduced amount of sulfur or sulfur compounds relative to the sulfur or sulfur compounds present in the hydrocarbon feedstream prior to contact with the fluidizable catalyst, wherein the reduced amount of sulfur or sulfur compounds is less than 50 percent of the amount of sulfur or sulfur compounds in the hydrocarbon feedstream prior to contact with the fluidizable catalyst;

separating the desulfurized crude olefin product from the fluidizable catalyst onto which at least a portion of the sulfur or sulfur compounds is absorbed;

regenerating at least a portion of the fluidizable catalyst in a combustion portion of a regenerator, wherein the combustion portion comprises an upflow reactor with a net upward flow of fluidized catalyst and gases or counterflow configuration with a net upward flow of air and fuel and downward flow of fluidized catalyst; and treating the fluidizable catalyst with an oxygen-containing gas for at least 2 minutes.

2. The method of claim 1, wherein regenerating occurs at a temperature within a range of from 550° centigrade to 800° centigrade.

3. The method of claim 1, wherein the reactor operates at a weight hourly space velocity (WHSV) within a range of from 0.1 $hr^{-1}$ to 1000 $hr^{-1}$.

4. The method of claim 1, wherein the combustion portion of the regenerator operates with a weight hourly space velocity within a range of from 0.5 $hr^{-1}$ to 1000 $hr^{-1}$ as calculated by a sum of a mass of air and fuel divided by a mass of adsorbent/catalyst in the combustion portion.

5. The method of claim 1, wherein the catalyst support is alumina-silica with an alumina content within a range of from 90 to 99.5 percent by weight and a silica content within a range of from 0.5 to 10 percent by weight, both percentages being based upon total catalyst support weight and, when added together, total 100 percent by weight.

6. The method of claim 5, wherein the alumina content is within a range of from 97 to 99.5 percent by weight and the silica content is within a range of from 0.5 to 3 percent by weight, both percentages being based upon the total catalyst support weight and, when added together, total 100 percent by weight.

7. The method of claim 1, wherein the amount of sulfur or sulfur compounds in the hydrocarbon feedstream prior to contact with the fluidizable catalyst causes a drop in catalyst dehydrogenation activity over an average catalyst residence time within a range of from 0.1 minute to 10 minutes of less than 30 percent versus an equivalent case with no sulfur in the hydrocarbon feedstream as measured by fixed bed experimental results.

8. The method of claim 1, wherein treating the fluidizable catalyst with oxygen for at least 2 minutes is performed after regenerating the fluidizable catalyst in the combustion portion of the regenerator.

9. The method of claim 1, wherein the oxygen-containing gas is air.

10. The method of claim 1, wherein the catalyst support comprises from 0.01 to 5 percent by weight alkali or alkaline earth element.

11. The method of claim 1, wherein the catalyst support comprises from 0.01 to 5 percent by weight potassium.

12. The method of claim 1, wherein the amount of sulfur or sulfur compounds in the hydrocarbon feedstream prior to contact with the fluidizable catalyst is within a range of from at least 1 part by weight per million parts by weight of hydrocarbon feedstream to less than 123 parts by weight per million parts by weight of hydrocarbon feedstream.

13. The method of claim 1, wherein the sulfur or sulfur compounds are not removed from the hydrocarbon feedstream before contacting the hydrocarbon feedstream with the fluidizable catalyst.

14. The method of claim 1, further comprising removing the sulfur species from a regenerator effluent.

15. The method of claim 14, wherein the sulfur species are removed from the regenerator effluent by contacting the regenerator effluent with a scrubbing agent.

16. The method of claim 1, wherein the fluidizable catalyst is contacted with the hydrocarbon feedstream in at least one of a riser reactor, a fast fluidized reactor, a turbulent bed reactor, or a bubbling bed reactor.

17. The method of claim 1, wherein the fluidizable catalyst consists of:

the alumina or alumina-silica catalyst support;
the gallium;
the platinum;
optionally an alkali or alkaline earth metal; and
optionally a promotor metal selected from the group consisting of zinc, molybdenum, and copper.

* * * * *